US006716186B1

(12) United States Patent
Singh et al.

(10) Patent No.: US 6,716,186 B1
(45) Date of Patent: Apr. 6, 2004

(54) CURABLE ADHESIVE SPLINTS AND METHODS

(75) Inventors: Balbir Singh, Singapore (SG); Lim Fang Pek, Singapore (SG); Kurt Allenberg, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/640,353

(22) Filed: Aug. 16, 2000

(51) Int. Cl.$^7$ .................................................. A61F 5/00
(52) U.S. Cl. ................................. 602/22; 602/6; 602/8
(58) Field of Search ..................... 602/5–8, 22, 41–42, 602/52, 54–58, 75, 900, 904; 128/858, 880, 848

(56) References Cited

U.S. PATENT DOCUMENTS

| | | |
|---|---|---|
| RE24,906 E | 12/1960 | Ulrich |
| 3,389,827 A | 6/1968 | Abere et al. |
| 3,594,813 A * | 7/1971 | Sanderson .................. 128/858 |
| 4,112,213 A | 9/1978 | Waldman |
| 4,161,175 A | 7/1979 | Bentele |
| 4,169,469 A | 10/1979 | Arluck |
| 4,502,479 A | 3/1985 | Garwood et al. |
| 4,628,917 A * | 12/1986 | Campagna, Jr. ............... 602/6 |
| 4,683,877 A | 8/1987 | Ersfeld et al. |
| D291,830 S | 9/1987 | Murtaugh, III et al. |
| 4,928,712 A * | 5/1990 | Mele ........................... 128/879 |
| 4,946,726 A * | 8/1990 | Sandvig ..................... 602/8 X |
| D310,883 S | 9/1990 | Ellis |
| 4,968,542 A | 11/1990 | Gasper et al. |
| 4,982,744 A * | 1/1991 | Stanec ......................... 128/879 |
| 5,197,943 A | 3/1993 | Link |
| 5,230,699 A | 7/1993 | Grasinger |
| 5,354,259 A | 10/1994 | Scholz et al. |
| 5,397,298 A * | 3/1995 | Mazza .......................... 602/75 |
| 5,423,735 A | 6/1995 | Callinan et al. |
| 5,520,621 A * | 5/1996 | Edenbaum ..................... 602/8 |
| 5,531,855 A * | 7/1996 | Heinecke ..................... 156/252 |
| 5,571,079 A * | 11/1996 | Bello .......................... 602/46 |
| 5,577,999 A * | 11/1996 | Sekine .......................... 602/8 |

(List continued on next page.)

FOREIGN PATENT DOCUMENTS

| | | |
|---|---|---|
| EP | 0 235 949 | 9/1987 |
| WO | WO 94/27648 | 12/1994 |
| WO | WO 99/13865 | 3/1999 |
| WO | WO 99/13866 | 3/1999 |
| WO | WO 99/27975 | 6/1999 |
| WO | WO 00/14131 | 3/2000 |
| WO | WO 00/32142 | 6/2000 |

OTHER PUBLICATIONS

Logghe, *3M Scotchcast Thermoplastic Material Handleiding voor de meest voorkomende toepassingen*, The Netherlands, 84 pages and English Language translation, *3M Scotchcast Thermoplastic Material Manual for the most common applications*, 61 pages, Publication Date was more Than 1 Year Earlier Than Aug. 16, 2000.
(Admitted by Applicant). The Publication Date was on or Before Aug. 15, 1999.

*Primary Examiner*—Nicholas D. Lucchesi
*Assistant Examiner*—Quang D Thanh
(74) *Attorney, Agent, or Firm*—Nancy M. Lambert

(57) ABSTRACT

Curable adhesive splints, methods of manufacturing the splints and methods of using the splints are disclosed. The splints include a curable splinting layer and an exposed pressure sensitive adhesive proximate a first major side of the splinting layer. The pressure sensitive adhesive is used to secure the curable layer in position to provide the desired immobilization. The curable splinting layer may be of any material that can be shaped and cured to provide the desired level of stiffness required for immobilization, such as, e.g., moisture-curable splinting material, etc. The curable adhesive splints may be molded or formed to a desired shape while still providing the stiffness required for immobilization after curing.

34 Claims, 4 Drawing Sheets

U.S. PATENT DOCUMENTS

| | | |
|---|---|---|
| 5,593,628 A | 1/1997 | Scholz et al. |
| 5,614,310 A | 3/1997 | Delgado et al. |
| 5,682,607 A * | 11/1997 | Klein .................... 128/858 X |
| 5,713,838 A | 2/1998 | Termanini ...................... 602/8 |
| 5,755,678 A * | 5/1998 | Parker .......................... 602/6 |
| 5,807,295 A * | 9/1998 | Hutcheon .................... 602/42 |
| 5,976,610 A | 11/1999 | Scholz et al. |
| 5,997,492 A | 12/1999 | Delmore et al. |
| 6,030,355 A | 2/2000 | Callinan et al. |
| 6,171,985 B1 * | 1/2001 | Joseph ....................... 442/346 |

\* cited by examiner

CURABLE ADHESIVE SPLINTS AND METHODS

FIELD OF THE INVENTION

The present invention relates to the field of orthopedic splinting devices. More particularly, the present invention provides curable adhesive splints including a curable splinting layer and an exposed pressure sensitive adhesive for retaining the splint in position on a patient.

BACKGROUND

Immobilization of various portions of human and animal bodies is required to allow for proper healing of skeletal fractures or other injuries. Where the fracture is in a limb, e.g., arm or leg, immobilization techniques typically include wrapping the injured limb with a curable casting/splinting material that hardens to reduce the fracture and thus allow for proper healing.

Immobilization of smaller skeletal features, such as fingers (after fracture, ligament repair, etc.) or of oddly shaped skeletal features, such as noses, pose a more difficult challenge. Finger fractures may be reduced surgically by the insertion of pins, etc. Surgical intervention, however, results in soft-tissue trauma and the risk of post-surgery infection is present.

Finger fractures may also be immobilized by securing aluminum, wood or plastic strips to the finger by wrapping gauze and adhesive tape around the finger. Noses may be immobilized by using a curable material, e.g., plaster of Paris, shaped to provide the desired support.

In both situations, the immobilization techniques are cumbersome and difficult to accomplish. They require a care provider to assemble multiple individual components. In the case of finger splints, the care provider is required to position the splinting components as desired while simultaneously securing them in position. This combination of activities can prove difficult to accomplish without impairing the most effective positioning of the splints or their secure attachment, both of which can ultimately impact the effectiveness of the immobilization.

Another disadvantage is that, where aluminum or other metallic splints are used, the ability to monitor healing by radiography may be adversely impacted due to obstruction by the metallic splints.

An additional disadvantage is that the resulting splint constructions are bulky. The cumbersome finger splints may excessively impair the wearer's ability to button or unbutton clothing, open and close buckles, wear gloves, and to accomplish tasks such as typing, etc. In the case of nasal splints, the patient's ability to wear eyeglasses can be impaired. Furthermore, the cosmetic appearance can pose a barrier to effective use of the splint as patients may be motivated to remove the splint early because of appearance.

SUMMARY OF THE INVENTION

The present invention provides adhesive splints, methods of manufacturing the splints and methods of using the splints. The splints include a curable splinting layer and an exposed pressure sensitive adhesive proximate a first major side of the splinting layer. The pressure sensitive adhesive is used to secure the curable layer in position to provide the desired immobilization. The curable splinting layer may be of any material that can be shaped and cured to provide the desired level of stiffness required for immobilization, such as, e.g., moisture-curable splinting material, etc.

One advantage of the adhesive splints of the present invention is the ability to mold or form the splint to a desired shape while still providing the stiffness required for immobilization after curing. The shaped splinting layer can reduce the bulk of the finished splint.

Another advantage is that the splints may be provided as a one-piece, integral unit, thereby simplifying positioning and attachment of the splint as compared to known splinting techniques that use multiple individual components. For example, in some embodiments of the adhesive splints of the invention, the splinting layer may be attached directly to the patient's skin, eliminating the need for an underlying layer of bandaging. In addition, the splinting layer is not separate from the materials used to secure the splint, thus preventing the need to hold the splint in place while wrapping it with adhesive tape.

In some embodiments, the splints allow for ambulation or micro-motion of, e.g., an immobilized finger, thereby reducing stiffness associated with total immobilization of the finger. As a result, the need for rehabilitation to restore complete range of motion after immobilization may be reduced. Although some small amount of motion may be allowed, such restraint is still considered "immobilization" as that term is used in connection with the present invention.

The adhesive splints of the present invention are also preferably radiolucent, thereby providing the opportunity to monitor the healing process without removing the splint.

The adhesive splints of the present invention may also preferably be manufactured of porous materials, thereby improving patient comfort during immobilization.

The adhesive curable splint of the present invention may optionally be provided in a package. In some instances, the curable splinting layer may include moisture-curable resin and the package may be moisture proof to prevent curing of the splint until desired.

In one aspect, the present invention provides a curable adhesive splint having an interior surface and an exterior surface, the splint including a curable splinting layer having first and second major sides, wherein the first major side of the splinting layer is proximate the interior surface of the splint; and exposed pressure sensitive adhesive proximate at least a portion of the interior surface of the splint, such that the splint can be adhesively attached to a patient's skin.

In another aspect, the present invention provides a curable adhesive splint having an interior surface and an exterior surface, the splint including a backing layer proximate the exterior surface of the splint; a padding layer proximate the interior surface of the splint; a curable splinting layer retained between the backing layer and the padding layer; and exposed pressure sensitive adhesive on at least a portion of the interior surface of the splint, such that the splint can be adhesively attached to a patient's skin.

In another aspect, the present invention provides a method of manufacturing an adhesive curable splint having an interior surface and an exterior surface by providing a curable splinting layer including first and second major sides, wherein the first major side is proximate the interior surface of the splint; providing exposed pressure sensitive adhesive proximate the interior surface of the splint, such that the splint can be adhesively attached to a patient. The method may optionally also include locating a padding layer over the first major side of the curable splinting layer; locating a backing layer over the second major side of the curable splinting layer; and retaining the curable splinting layer between the padding layer and the backing layer.

In another aspect, the present invention may provide a method of using a curable adhesive splint having an interior surface and an exterior surface by providing an adhesive splint including a curable splinting layer having first and second major sides, wherein the first major side of the splinting layer is proximate the interior surface of the splint, the splint further including exposed pressure sensitive adhesive proximate at least a portion of the interior surface of the splint; adhesively attaching the splint to a patient with the exposed pressure sensitive adhesive; and curing the curable splinting layer.

These and other features and advantages of the present invention are described more completely below with respect to illustrative embodiments of the invention.

DETAILED DESCRIPTION OF ILLUSTRATIVE EMBODIMENTS OF THE INVENTION

The present invention provides adhesive splints, methods of manufacturing the splints and methods of using the splints. The adhesive splints may be useful in connection with treatment of both humans and animals, although the embodiments described below may be primarily adapted for use on humans. In addition, the adhesive splints may be used at a variety of locations on the body, although the splints may be particularly advantageous when used on fingers, toes, noses, and other small skeletal features. The illustrative embodiments described below are adapted for use on fingers and noses, but the adhesive splints of the present invention should not be limited to finger and nasal splints.

Figure 1:
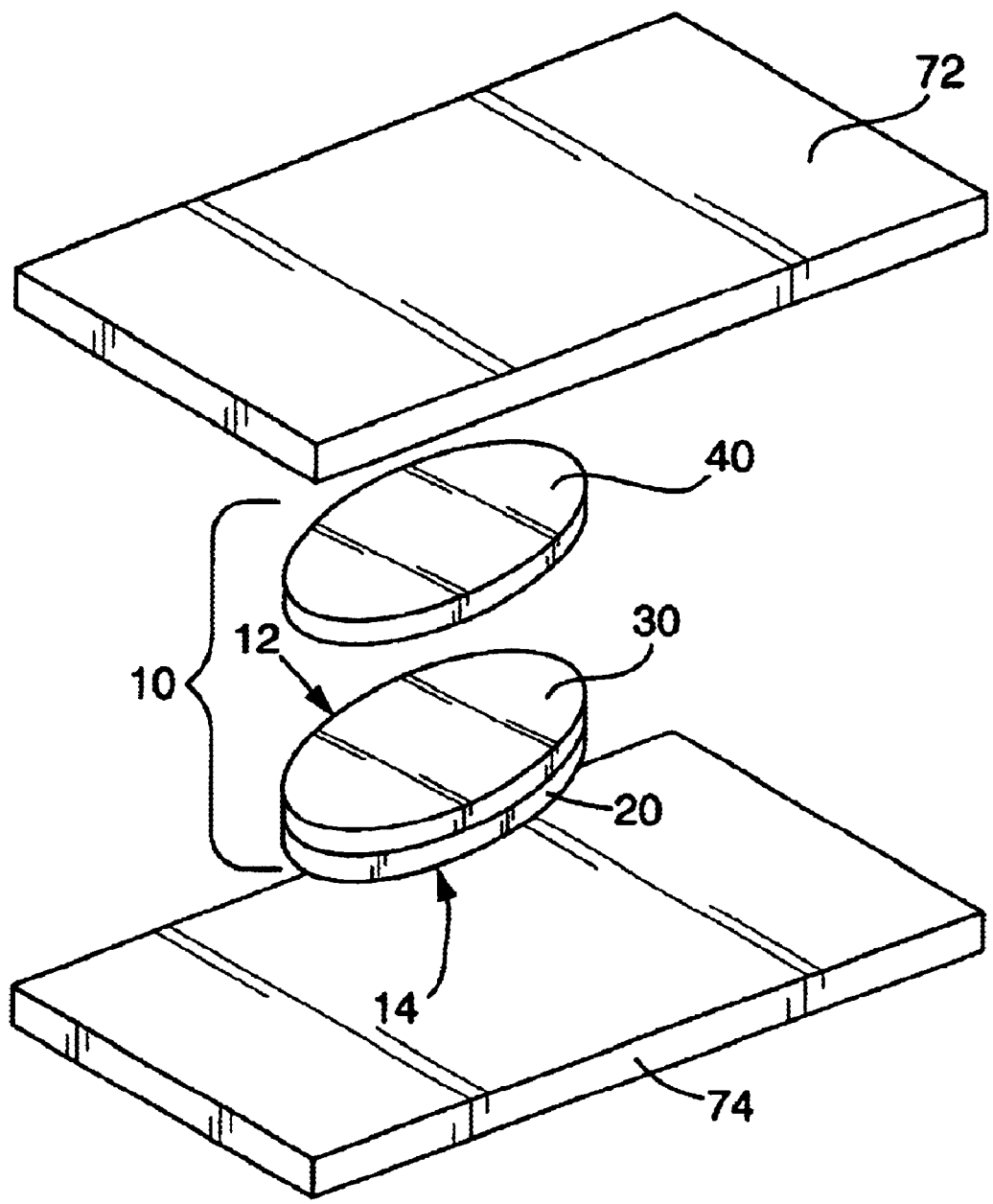
FIG. 1 is an exploded perspective view of one adhesive splint according to the present invention.

FIG. 1 illustrates one adhesive splint according to the present invention. The splint 10 includes a curable splinting layer 20, a pressure sensitive adhesive 30, and an optional release liner 40 covering the adhesive 30 before application to a patient. The splint 10 includes an interior surface 12 that, when the splint 10 is attached, faces the patient. The splint 10 also includes an exterior surface 14 that faces away from the patient when the splint 10 is attached.

The curable splinting layer 20 may take a variety of forms. By "curable" it is meant that the splinting layer 20 can be shaped depending on the skeletal feature it is used to support or immobilize followed by curing to form a rigid or self-supporting shape. The term "curing" is used herein to refer to reactive systems that irreversibly solidify upon the application of heat and/or other sources of energy, such as E-beam, ultraviolet, visible, etc., or with time upon the addition of a chemical catalyst, moisture, and the like. The irreversible solidification may involve polymerization, crosslinking, or both.

It may be preferred that the curable splinting layer be provided as the combination of a moisture-curable resin carried by a supporting layer. Examples of curable splinting materials that include a moisture-curable resin and a support layer are described in U.S. Pat. No. 4,502,479 (Garwood et al.); U.S. Pat. No. 4,683,877 (Ersfeld et al.); U.S. Pat. No. 4,968,542 (Gasper et al.); U.S. Pat. No. 5,354,259 (Scholz et al.); U.S. Pat. No. 5,423,735 (Callinan et al.); U.S. Pat. No. 5,593,628 (Scholz et al.); U.S. Pat. No. 5,976,610 (Scholz et al.); U.S. Pat. No. 5,997,492 (Delmore et al.); and U.S. Pat. No. 6,030,355 (Callinan et al.). The number of layers of the resin-filled splinting/casting materials and their shape or shapes may be varied to provide the desired strength to the finished splint.

It may also be preferred that the curable splinting layer 20 be radiolucent to a sufficient degree to allow for radiographic monitoring of the skeletal features underlying the splint 10 when in position on a patient. The moisture-curable resin splinting materials described in the references listed above are typically considered to be radiolucent.

It may also be preferred that the splinting layer 20 be porous to allow moisture vapor escaping from the skin beneath the splint 10 to escape. For curable splinting materials that include a moisture-curable resin and support layer, it may be preferred that the support layer provide pores such that after the resin cures, moisture vapor can pass through the splinting layer 20.

The pressure sensitive adhesive 30 is provided to secure the splint 10 in location on a patient. In the depicted embodiment, the pressure sensitive adhesive 30 is provided in a manner that results in direct contact between the pressure sensitive adhesive 30 and the patient's skin. In those situations the pressure sensitive adhesive 30 is preferably skin compatible.

Suitable pressure sensitive adhesives include the standard skin-compatible adhesives such as those described in U.S. Pat. No. Re. 24,906 (Ulrich), particularly a copolymer of 96% iso-octyl acrylate units and 4% acrylamide units and a copolymer of 94% iso-octyl acrylate units and 6% acrylic acid units. Other useful adhesives are those described in U.S. Pat. No. 3,389,827 (Abere et al.) that include block copolymers having three or more polymer block structures having a general configuration -A-B-A- wherein each A is a thermoplastic polymer block with a glass transition temperature above room temperature (i.e., above about 20° C.) having an average molecular weight between about 5000 and 125,000 and B is a polymer block of a conjugated diene having an average molecular weight between about 15,000 and 250,000. Additional examples of useful adhesives are acrylic adhesives such as iso-octyl acrylate/n-vinyl pyrrolidone copolymer adhesives and crosslinked acrylate adhesives such as for example those described in U.S. Pat. No. 4,112,213 (Waldman). The pressure sensitive adhesive 30 may be present on the splinting layer 20 as a continuous layer (as shown in FIG. 1) or as a patterned layer (not shown), e.g., as non-continuous adhesive stripes.

The pressure sensitive adhesive 30 may optionally be a microsphere adhesive with low skin trauma properties as described in U.S. Pat. No. 5,614,310 (Delgado et al.); a fibrous pressure sensitive adhesive with low trauma properties as described in International Publication No. WO 99/27,975 (Joseph et al.); or have especially good adhesion to wet skin, such as the adhesives described in International Publication No. WO 00/32142 (Lucast et al.), and International Application Nos. PCT/US99/13865 (Gieselman) and PCT/US99/13866 (Lucast et al.), both filed Jun. 18, 1999.

If the splinting layer 20 includes a curable resin, it may be desirable to prevent skin contact or reduce the amount of skin contact with the resin before and/or during curing. As a result, it may be preferred that the pressure sensitive adhesive 30 provide barrier properties in addition to adhering to the patient. For example, the pressure sensitive adhesive 30 may be thick enough to effectively reduce or prevent skin contact with the resin (particularly where the pressure sensitive adhesive 30 is porous).

The illustrated splint 10 also includes an optional release liner 40 to protect the pressure sensitive adhesive 30 from, e.g., contamination, before the splint is applied to a patient. The release liner 40 may be made of or coated with any suitable release material, e.g., silicone, polytetrafluoroethylene (PTFE), etc. that is matched to the pressure sensitive adhesive 30 according to known principles.

Also illustrated in FIG. 1 are an upper layer 72 and a lower layer 74 that, when attached together about the periphery of the splint 10, form an optional package in which the splint 10 can be located before use. The resulting package may preferably be moisture-proof when the curable splinting layer 20 includes a moisture-curable resin. FIG. 1 illustrates only one embodiment of a package and many varieties of moisture-proof packages (and corresponding methods of manufacturing them) are known and will not be further described herein. Also, although only one splint 10 is illustrated as being located within the package formed by packaging layers 72 and 74, two or more splints could be located within a single package if so desired.

Figure 2:
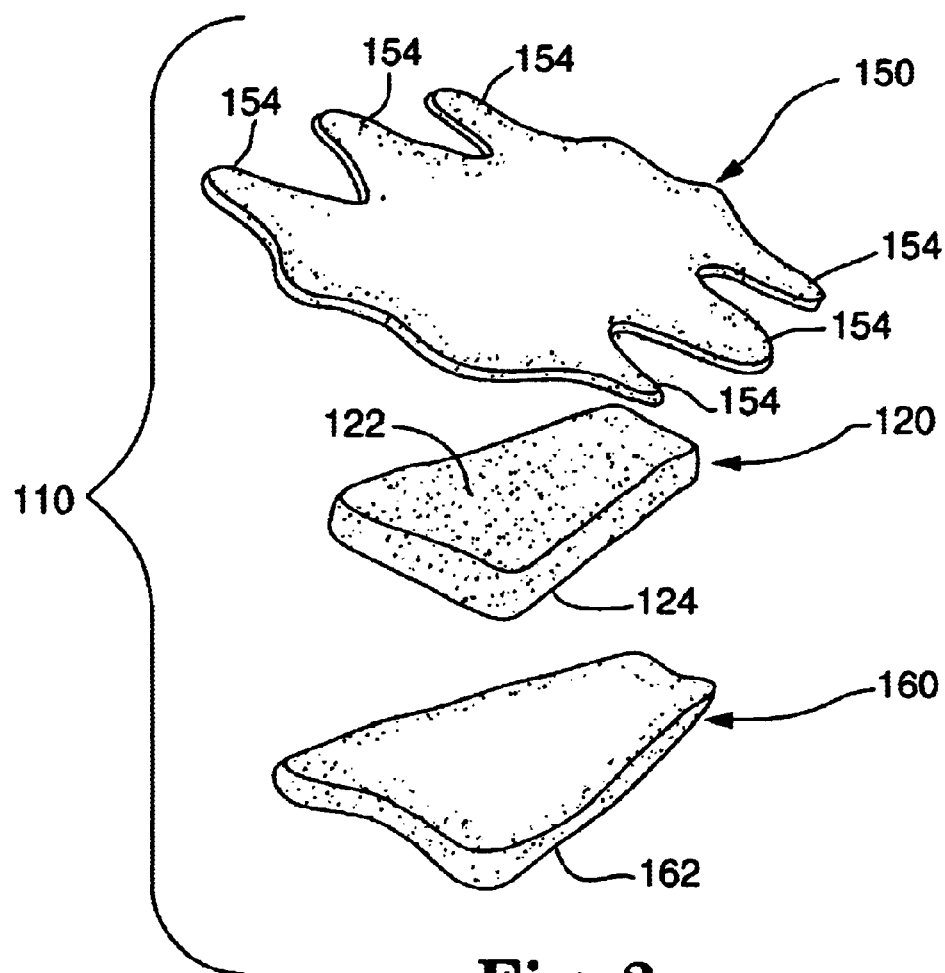
FIG. 2 is an exploded perspective view of another adhesive splint according to the present invention.
Figure 3:
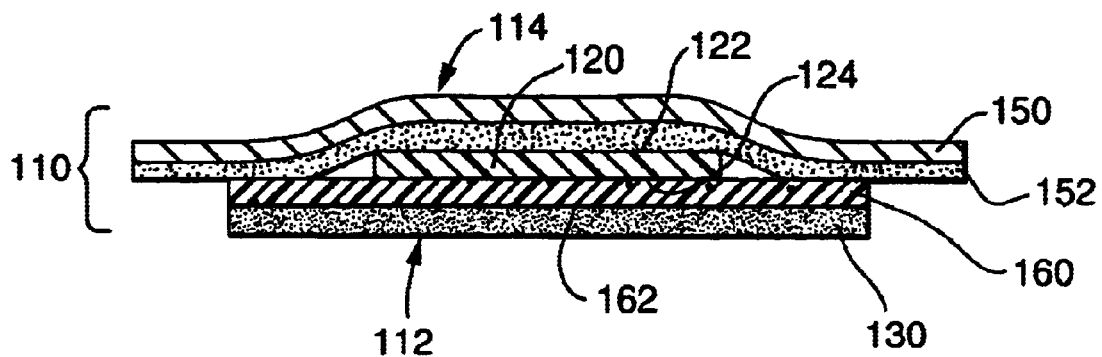
FIG. 3 is a cross-sectional view of the adhesive splint of FIG. 2 illustrating the various layers of the adhesive splint.

FIG. 2 is an exploded diagram depicting another adhesive splint 110 according to the present invention and FIG. 3 is a cross-sectional view of the splint 110 as assembled. The splint 110 includes a curable splinting layer 120, optional backing layer 150, optional padding layer 160 and exposed pressure sensitive adhesive 130.

The backing layer 150 may be made of a variety of materials including films, sheets, foams, nonwoven fabrics, woven fabrics, etc. It may be preferred that the backing layer 150 be porous to allow the passage of moisture vapor and or water. Other potential characteristics of the backing layer 150 are barrier properties (to prevent or reduce migration of a curable resin from the splinting layer 120, if such a resin is present); resistance to soiling; durability, strength, toughness, limited extensibility, etc. It may be preferred that the backing layer 150 be made of a nonwoven fibrous material. It may also be preferred that the backing layer 150 be permeable to liquid water, e.g., to enable water applied to the exterior surface 114 of the splint 110 to reach a moisture-curable splinting layer 120. Examples of some suitable materials for the backing layer 150 are described in, e.g., International Publication No. WO 94/27648 (Campagna et al.)

The padding layer 160 may be made of a variety of materials including films, sheets, foams, nonwoven fabrics, woven fabrics, etc. It may be preferred that the padding layer, 160 be porous to allow the passage of moisture vapor. It may also be preferred that the padding layer 160 be compressible, i.e., that it conform to irregular surfaces when placed in compression. Examples of suitable compressible materials include, but are not limited to, foams, felts, etc. Other potentially desirable characteristics of the padding layer 160 are barrier properties (to prevent or reduce migration of a curable resin from the splinting layer 120, if such a resin is present); resistance to soiling; durability, strength, toughness, limited extensibility, etc. Like the backing layer, International Publication No. WO 94/27648 (Campagna et al.) also describes materials that may be useful as a padding layer 160 in connection with the present invention.

The backing layer 150 may be attached to the outer surface 122 of the splinting layer 120 by, e.g., an adhesive 152 or by any other suitable technique. Alternatively, the backing layer 150 may be merely located over the outer surface 122 of the splinting layer 120. Where the backing layer 150 is not attached to the splinting layer 120, both the backing layer 150 and the padding layer 160 are preferably larger than the splinting layer 120, i.e., both the backing layer 150 and the padding layer 160 extend beyond the periphery of the splinting layer 120. As a result, the larger backing layer 150 and padding layer 160 envelop or enclose the curable splinting layer 120.

Where both the backing layer 150 and padding layer 160 are larger than the splinting layer 120, it is preferred that the backing layer 150 and padding layer 160 are attached to each other about at least a portion of the periphery of the splinting layer 120. Where the backing layer 150 and the padding layer 160 are not continuously attached to each other about the entire periphery of the splinting layer 120, it may be preferred that the layers 150 and 160 be attached in portions that are sufficient to capture the splinting layer 120, especially where neither the backing layer 150 nor the padding layer 160 are directly attached to the splinting layer 120. Alternatively, it may be preferred that the backing layer 150 and padding layer 160 be attached to each other continuously around the entire periphery of the splinting layer 120.

The backing layer 150 and padding layer 160 may be attached to each other about the periphery of the splinting layer 120 by any suitable technique or combination of techniques. Examples may include, but are not limited to adhesives (see layer 152 in FIG. 3), welding, mechanical fasteners, sewing, etc. Alternatively, it may be preferred that only one of the backing layer 150 and padding layer 160 extend beyond the periphery of the splinting layer 120. Where only the padding layer 160 extends beyond the periphery of the splinting layer 120, the padding layer 160 is preferably attached to the inner surface 124 of the splinting layer 120 by any suitable technique or combination of techniques. In such a construction, the backing layer 150 is attached to the outer surface 122 of the splinting layer 120. Examples of suitable attachment techniques may include, but are not limited to adhesives, welding, mechanical fasteners, sewing, etc.

Where only the backing layer 150 extends beyond the periphery of the splinting layer 120, the backing layer 150 is preferably attached to the outer surface 122 of the splinting layer 120 by any suitable technique or combination of techniques. In such a construction, the padding layer 160 is attached to the inner surface 124 of the splinting layer 120. Examples of suitable attachment techniques may include, but are not limited to adhesives, welding, mechanical fasteners, sewing, etc. In some embodiments, the moisture-curable or other curable resin, if present in the splinting layer 120, can function to enhance the adherence of the splinting layer 120 to the padding layer 160 and/or the backing layer 150.

In the embodiment depicted in FIGS. 2 and 3, both the backing layer 150 and the padding layer 160 extend beyond the periphery of the splinting layer 120. In addition, the backing layer 150 extends beyond the periphery of the padding layer 160. In addition, the backing layer 150 includes tabs 154 extending from opposing sides of the splint 110.

It may be preferred that the surface of the tabs 154 facing the splinting layer 120 include a pressure sensitive adhesive 152 to facilitate attachment of the splint 110 to a patient as will be described in more detail below. Although the pressure sensitive adhesive 152 is the same pressure sensitive adhesive used to attach the backing layer 150 to the padding layer 160 and the splinting layer 120 in the depicted embodiment, the tabs 154 may be coated with a different pressure sensitive adhesive if so desired. If the pressure sensitive adhesive 152 may come into contact with the patient, it may be preferred that the pressure sensitive adhesive be skin-compatible. The composition of the pressure sensitive adhesive 152 may, for example, be selected from those described above with respect to the pressure sensitive adhesive 30 used in splint 10

Although the tabs 154 are depicted as integral extensions of the backing 150, it may also be possible to provide tabs 154 that are formed of a material different than the majority of the backing 150. In another alternative, the tabs 154 may be formed of an additional layer of the same material used for a majority of the backing layer 150.

In yet another variation, it may be possible that both the backing layer 150 and the padding layer 160 extend beyond the periphery of the splinting layer 120. In this variation, however, the padding layer 160 may extend beyond the periphery of the backing layer 150 and include tabs that extend from opposing sides of the splint 110.

It may further be preferred that an exposed pressure sensitive adhesive 130 be provided on the surface of the splint 110 that faces the patient when the splint 110 is in use. Such a pressure sensitive adhesive 130 may be advantageous in securing the splint 110 in position on the patient while the curable splinting layer 120 is curing. Furthermore, the pressure sensitive adhesive 130 may provide additional barrier properties to those provided by the padding layer 160 to prevent or reduce skin contact with any resin used in the splinting layer 120.

The composition of the pressure sensitive adhesive 130 may be selected from those described above with respect to the pressure sensitive adhesive 30 used in splint 10. The pressure sensitive adhesive 130 may be provided over the entire inner surface 162 of the padding layer 160 or over only a portion of the inner surface 162 of the padding layer 160. In some embodiments, the inner surface 162 of the padding layer 160 may be free of any pressure sensitive adhesives, with the only exposed pressure sensitive adhesive being that located on the larger backing layer 150. In such a design, only the pressure sensitive adhesive 152 on the portion of the larger backing layer 150 will be exposed outside of the periphery of the padding layer 160.

For the purposes of the present invention, the adhesives, e.g., layers 152 and 130, are depicted as continuous layers over their respective portions of the backing 150 or padding 160. The adhesives, may however, be pattern-coated or otherwise supplied as non-continuous layers.

The splint 110 may be provided with a release liner (not shown) to protect the pressure sensitive adhesive 130 and pressure sensitive adhesive 152 on exposed tabs 154. If desired a multi-part liner may be used to protect different portions of the exposed pressure sensitive adhesives in a manner that may be useful to assist with application of the splint 110. For example a central liner may be provided over the pressure sensitive adhesive 130 and separate liners provided on each side to protect the exposed pressure sensitive adhesive 152 on the tabs 154 of the backing layer 150. The liners may incorporate tabs, J-folds, and other features as desired.

Figure 4:
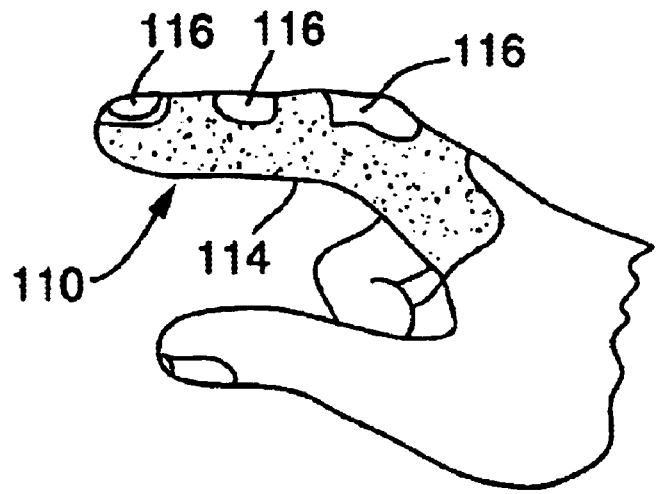
FIGS. 4 & 5 are views of the adhesive splint of FIGS. 2 & 3 in location on a finger.
Figure 5:
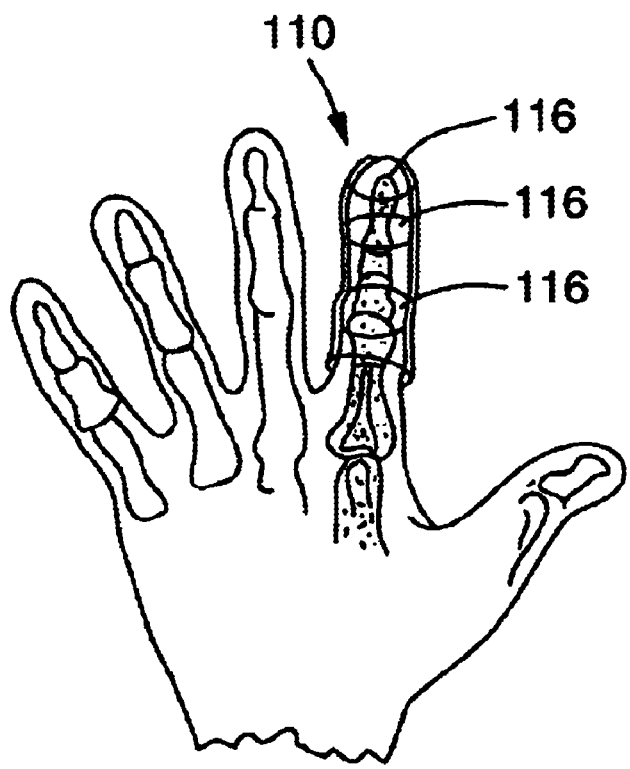

The splint 110 of FIGS. 2 and 3 is illustrated in position on a human finger in FIGS. 4 and 5. The body or major portion of the splint 110 including the splinting layer (not shown) is located on the anterior surface of the finger, with the tabs 154 wrapping around the posterior surface of the finger. Optionally, one or more of the tabs 154 may overlap the corresponding opposing tabs 154 such that only the tabs 154 on one side of the splint 110 come into contact with the skin.

Referring back to, e.g., FIGS. 2 and 3, it may be preferred that the splinting layer 120 be wide enough such that when applied to a finger or other elongated skeletal feature, e.g., toe, arm, leg, etc., the splinting layer 120 takes on a curved shape. By providing a splinting layer 120 with a curved profile, the strength of the splint 110 may be improved (where strength refers to the resistance of the splint 110 to bending forces). In addition, resistance of the splint 110 to loads directed transverse to, e.g., the finger, may also be improved when the splinting layer 120 takes on a curved profile as applied.

An additional potentially advantageous feature of the splint 110 illustrated in FIGS. 4 and 5 is that by providing voids 116 in the splint 110 as applied, patient comfort may be enhanced. Additionally, the overall profile or size of the splint 110 is further reduced by limiting the amount of material located on the posterior surface of the finger.

Figure 6:
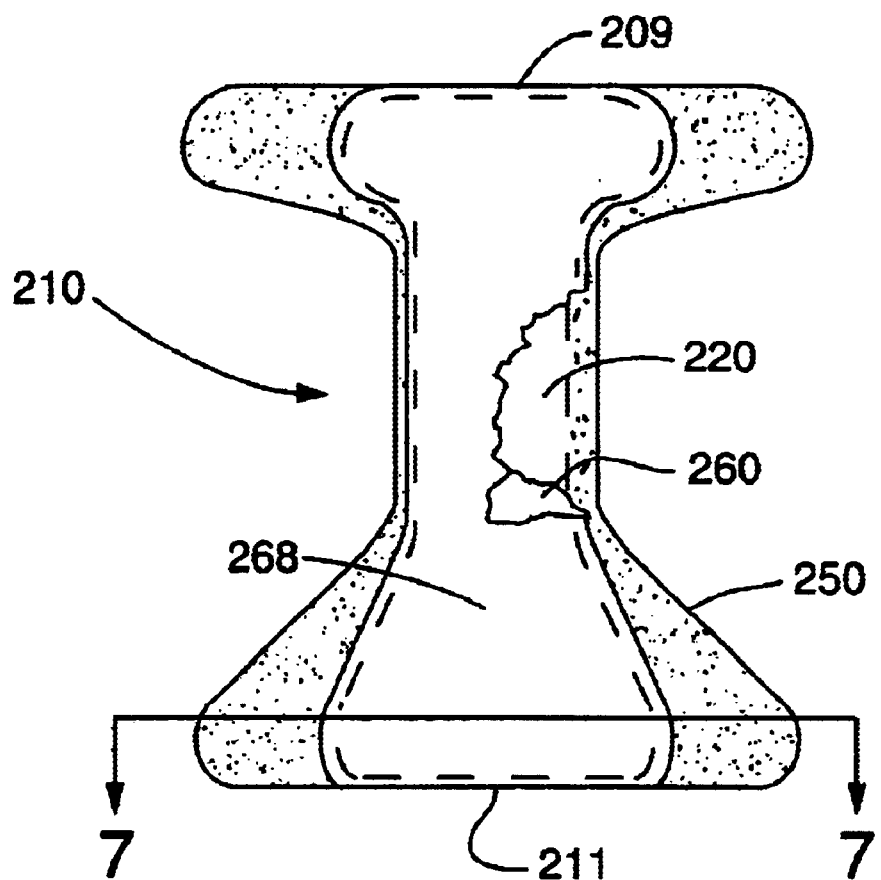
FIG. 6 is a plan view of another adhesive splint of the present invention.
Figure 7:
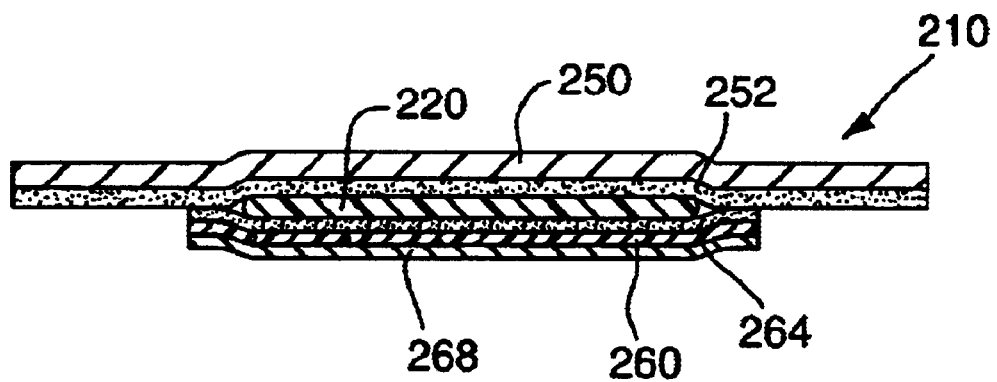
FIG. 7 is an enlarged cross-sectional view of the splint of FIG. 6 taken along line 7—7 in FIG. 6.

FIGS. 6 and 7 depict an illustrative nasal splint 210 according to the present invention. The splint 210 includes a splinting layer 220, optional backing layer 250, and optional padding layer 260. The various layers and their constructions are largely similar to those described above with respect to the splints 10 and 110 above. The curable splinting layer 220 is located between the backing layer 250 and the padding layer 260 (a portion of which is cut-away to expose the curable splinting layer in FIG. 6). The backing layer 250 includes a layer of a pressure sensitive adhesive 252 facing the splinting layer 220. Those portions of the pressure sensitive adhesive 252 located outside the periphery of the padding layer 260 are preferably exposed to facilitate attachment of the splint 210 to a patient.

The padding layer 260 also preferably includes a pressure sensitive adhesive 264 facing the splinting layer 220 and the backing layer 250. The pressure sensitive adhesive 264 facilitates attachment of the padding layer 260 to the backing layer 250 about the periphery of the splinting layer 220. Although depicted as being coextensive with the padding layer 260, the pressure sensitive adhesive 264 may be limited to the edges of the padding layer such that the padding layer 260 is not adhesively attached to the splinting layer 220.

The splint 210 may preferably have a wider portion at its upper end 209 which, when the splint 210 is applied to a patient, is located above the eyes on the forehead. The wider portion on the upper end 209 may provide additional resistance to twisting of the splint 210 when in use. It may also be preferred that the lower end 211 of the splint 210 be wider to bridge the lower portion of the patient's nose. In some instances, it may be desired that the splint 210 reach to the bony portion of the eye sockets below each eye.

Also illustrated in FIGS. 6 and 7 is a spacing layer 268 located on the side of the padding layer 260 facing away from the splinting layer 220 (i.e., towards a patient when the splint 210 is in position on the patient). The spacing layer 268 is partially cut-away in FIG. 6 to expose the underlying padding layer 260. The spacing layer 268 is provided in a manner that allows for its removal from between the splint 210 and the patient after the splint 210 is in position on the patient. The spacing layer functions to space the padding layer 260 from the surface of the patient's nose to improve comfort. Although the spacing layer 268 is depicted as coextensive with the padding layer 260, it may alternatively be provided in a narrower band that, e.g., extends along the bridge of the nose.

Examples of suitable materials for the spacing layer 268 include, but are not limited to, films, sheets, foams, nonwoven fabrics, woven fabrics, etc., that have a suitable thickness. It may be preferred that the spacing layer 268 be compressible, i.e., that it conform to irregular surfaces when placed in compression. Examples of suitable compressible materials include, but are not limited to, foams, felts, etc. Another potentially desirable characteristic of the spacing layer 268 is prevention or reduction in the migration of a curable resin from the splinting layer 220, if such a resin is present.

In one method of using the splint 210, it would be applied to the patient using the exposed pressure sensitive adhesive 252. After the splint 210 is attached using pressure sensitive adhesive 252, the curable splinting layer 220 would be cured in the desired shape with the spacing layer 268 separating the interior surface of the splint 210 from the patient. After curing of the splinting layer 220, the spacing layer 268 would be removed by, e.g., sliding it from between the patient and the padding layer 260, such that the padding layer 260 is spaced from the surface of the patient's nose in those areas where the spacing layer 268 was present during curing.

In an alternative method of using the splint 210, the splint 210 may be located over the patient's nose without attaching the pressure sensitive adhesive 252 to the patient (e.g., a protective liner could be provided over the pressure sensitive adhesive 252). The curable splinting layer 220 could then be shaped and cured as desired with the spacing layer 268 in position between the splint 210 and the patient. After curing, the splint 210 could be removed from the patient and the spacing layer 268 detached from the splint 210 to create the desired space when the splint 210 is attached to the patient using the pressure sensitive adhesive 252.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of this invention, and it should be understood that this invention is not limited to the illustrative embodiments set forth herein. Accordingly, the invention is to be limited only by the claims provided below.

EXAMPLES

The following examples are offered to aid in understanding of the present invention and are not to be construed as limiting the scope thereof. Unless otherwise indicated, all parts and percentages are by weight.

Example 1

Orthopedic Finger Splint

This example describes the construction and application of a multi-layered finger splint having a nonwoven backing layer, a water-curable splinting layer, and a padding layer.
Backing Layer An adhesive backing layer was constructed as described in Example 4 of International Publication No. WO 9927975 (Joseph et al.) and contained a polyacrylate-based blown microfiber pressure sensitive adhesive web with a basis weight of 60 g/m² laminated to a rayon/polyester (70/30) hydroentangled nonwoven web (SONTARA™ 8411, Dupont). A standard release liner was conventionally added to the adhesive side of the layer and the resulting backing layer was cut into a somewhat oval shape having three tapered tab segments extending from both lengthwise sides to enable ready adherence to a finger. (See FIG. 2). The backing layer (without release liner) was porous to liquid water.
Splinting Layer A splinting layer was constructed of a four-ply construction of water-curable resin-impregnated fiberglass casting tape (SCOTCHCAST™ Plus Casting Tape, 3M Company, St. Paul, Minn.) that was cut into a trapezoidal shape of a size slightly smaller in dimensions than the backing layer without the tab segments. (See FIG. 2).
Padding Layer A skin-contact padding layer including a conformable elastic foam pressure sensitive adhesive tape (MICROFOAM™ Tape, 3M Company) that was cut to a somewhat oval shape of the same size as the backing layer without the tab segments. (See FIG. 2).
Finger Splint Construction and Application A finger splint was constructed by placing the splinting layer on the center of the non-adhesive side of the padding layer and then centering the adhesive side (release liner removed) of the backing layer onto the splinting layer. The resulting laminate was pressed together using a rubber roller and a standard release liner was conventionally placed on the adhesive side of the completed finger splint.

The completed finger splint was applied to a finger by removing the release liner, placing the exposed adhesive on the padding layer against the finger, further securing with the tab segments of the backing layer, applying water to the backing layer, allowing the water to penetrate the backing layer and reach the splinting layer, gently molding the splint to the shape of the finger, and allowing the splinting layer to cure and harden. The resulting rigid splint was observed to be secure and comfortably worn on the finger.

Example 2

Orthopedic Finger Splint

A finger splint was constructed and applied as described in Example 1, except that the splinting layer contained SCOTCHCAST™ Soft Cast Casting Tape (3M Company) in place of the SCOTCHCAST™ Plus Casting Tape. The former is a water-curable resin-impregnated fiberglass casting tape that does not set to a completely rigid state, but that remains flexible even when completely cured. After application to a finger and curing, some movement, i.e., flexing, of the splinted finger was still possible.

Example 3

Orthopedic Finger Splint

A finger splint was constructed and applied as described in Example 1, except that in the final splint laminate construction the padding layer was inverted so that the adhesive side faced the splinting layer and the side of the padding layer facing the patient was free of adhesive.

Example 4

Orthopedic Finger Splint

A finger splint was constructed and applied as described in Example 1, except that the padding layer was coated with adhesive on both sides. The layer was made by coating the non-adhesive side of MICROFOAM™ Tape with a standard polyacrylate IOA/AA (94/6) skin adhesive.

Examples 5a–5b

Orthopedic Finger Splints

A finger splint (Example 5a) was constructed and applied as described in Example 1, except that the backing layer was cut into a rectangular shape having three rectangular tab segments extending from both lengthwise sides to enable ready adherence to a finger; the splinting layer was cut into a rectangular shape of a size slightly smaller in dimensions than the backing layer without the tab segments; and, the padding layer was cut into a rectangular shape of about the same size as the backing layer without the tab segments.

A finger splint (Example 5b) was constructed and applied as described in Example 1, except that the backing layer was cut into a rectangular shape having two tapered tab segments extending from both lengthwise sides to enable ready adherence to a finger; the splinting layer was cut into a rectangular shape of a size slightly smaller in dimensions than the backing layer without the tab segments; and, the padding layer was cut into a rectangular shape of about the same size as the backing layer without the tab segments.

What is claimed is:

1. A method of using a curable adhesive splint having an interior surface and an exterior surface, the method comprising:
   providing an adhesive splint comprising a backing layer proximate the exterior surface of the splint, a padding layer proximate the interior surface of the splint, and a curable splinting layer retained between the backing layer and the padding layer, wherein the backing layer and padding layer are attached to each other outside of the periphery of the curable splinting layer, the splint further comprising exposed pressure sensitive adhesive on at least a portion of the interior surface of the splint;
   adhesively attaching the splint to a patient with the exposed pressure sensitive adhesive; and
   curing the curable splinting layer.

2. A method according to claim 1, wherein the splint is cured while adhesively attached to the patient.

3. A method according to claim 1, further comprising opening a package containing the adhesive curable splint.

4. A method according to claim 3, wherein the curable splinting layer comprises a moisture-curable resin and the package comprises a moisture proof package.

5. A method of manufacturing an adhesive curable splint having an interior surface and an exterior surface, the method comprising:
   providing a curable splinting layer comprising first and second major sides, wherein the first major side is proximate the interior surface of the splint;
   providing exposed pressure sensitive adhesive proximate the interior surface of the splint, such that the splint can be adhesively attached to a patient;
   locating a padding layer over the first major side of the curable splinting layer;
   locating a backing layer over the second major side of the curable splinting layer;
   retaining the curable splinting layer between the padding layer and the backing layer; and
   attaching the backing layer and padding layer to each other outside of the periphery of the curable splinting layer.

6. A method according to claim 5, further comprising providing a release liner covering the pressure sensitive adhesive.

7. A method according to claim 5, wherein the pressure sensitive adhesive comprises a fibrous pressure sensitive adhesive.

8. A method according to claim 5, wherein the pressure sensitive adhesive is provided over substantially all of the interior surface of the splint.

9. A method according to claim 5, wherein the padding layer comprises a first side proximate the interior surface of the splint, and further wherein the pressure sensitive adhesive is located on at least a portion of the first side of the padding layer.

10. A method according to claim 5, further comprising locating the curable adhesive splint in a package.

11. A method according to claim 5, wherein the curable splinting layer comprises a moisture-curable resin and the package comprises a moisture proof package.

12. A curable adhesive splint having an interior surface and an exterior surface, the splint comprising:
    a backing layer proximate the exterior surface of the splint;
    a padding layer proximate the interior surface of the splint;
    a curable splinting layer retained between the backing layer and the padding layer;
    a spacing layer proximate the interior surface of the splint; and
    exposed pressure sensitive adhesive on at least a portion of the interior surface of the splint, such that the splint can be adhesively attached to a patient's skin.

13. A splint according to claim 12, wherein the padding layer comprises a first side proximate the interior surface of the splint, and further wherein the first side of the padding layer is substantially free of the exposed pressure sensitive adhesive.

14. A splint according to claim 12, wherein the padding layer comprises a first side proximate the interior surface of the splint, and further wherein the exposed pressure sensitive adhesive is located on at least a portion of the first side of the padding layer.

15. A splint according to claim 12, wherein the backing layer extends beyond a periphery of the curable splinting layer.

16. A splint according to claim 12, wherein the backing layer is adhesively attached to the curable splinting layer.

17. A splint according to claim 12, wherein the padding layer is adhesively attached to the curable splinting layer.

18. A splint according to claim 12, wherein the curable splinting layer comprises a moisture-curable resin.

19. A splint according to claim 12, further comprising a package containing the adhesive curable splint.

20. A splint according to claim 19, wherein the curable splinting layer comprises a moisture-curable resin and the package comprises a moisture proof package.

21. A curable adhesive splint having an interior surface and an exterior surface, the splint comprising:
    a backing layer proximate the exterior surface of the splint;
    a padding layer proximate the interior surface of the splint;
    a curable splinting layer retained between the backing layer and the padding layer; and
    exposed pressure sensitive adhesive on at least a portion of the interior surface of the splint, such that the splint can be adhesively attached to a patient's skin, wherein the backing layer and padding layer are attached to each other outside of the periphery of the curable splinting layer.

22. A splint according to claim 2, further comprising a release liner covering the exposed pressure sensitive adhesive before the splint is attached to the patient's skin.

23. A splint according to claim 21, wherein the pressure sensitive adhesive comprises a fibrous pressure sensitive adhesive.

24. A splint according to claim 21, wherein the pressure sensitive adhesive comprises a layer of the pressure sensitive adhesive proximate substantially all of the interior surface of the splint.

25. A splint according to claim 21, wherein the curable splinting layer comprises a moisture-curable resin.

26. A splint according to claim 21, wherein the padding layer comprises a first side proximate the interior surface of the splint, and further wherein the pressure sensitive adhesive is located on at least a portion of the first side of the padding layer.

27. A splint according to claim 21, wherein the padding layer comprises a first side proximate the interior surface of the splint, and further wherein the first side of the padding layer is substantially free of the exposed pressure sensitive adhesive.

28. A splint according to claim 27, wherein the pressure sensitive adhesive is located over substantially all of the first side of the padding layer.

29. A splint according to claim 21, wherein the padding layer comprises compressible material.

30. A splint according to claim 21, wherein the padding layer is adhesively attached to the curable splinting layer.

31. A splint according to claim 21, wherein the backing layer is adhesively attached to the curable splinting layer.

32. A splint according to claim 21, further comprising a spacing layer proximate the interior surface of the splint.

33. A splint according to claim 21, further comprising a package containing the curable adhesive splint.

34. A splint according to claim 33, wherein the curable splinting layer comprises a moisture-curable resin and the package comprises a moisture proof package.

* * * * *

UNITED STATES PATENT AND TRADEMARK OFFICE
CERTIFICATE OF CORRECTION

PATENT NO. : 6,716,186 B1
DATED : April 6, 2004
INVENTOR(S) : Singh, Balbir

It is certified that error appears in the above-identified patent and that said Letters Patent is hereby corrected as shown below:

Column 13,
Line 5, delete "2" and insert in place therefor -- 21 --.

Signed and Sealed this

Twentieth Day of September, 2005

JON W. DUDAS
*Director of the United States Patent and Trademark Office*